US005734827A

United States Patent [19]
Thornton et al.

[11] Patent Number: 5,734,827
[45] Date of Patent: Mar. 31, 1998

[54] DECONVOLUTION OF MLS RESPONSE DATA

[75] Inventors: Arthur Roger David Thornton, Southampton; John David Chambers, Nottingham; Timothy John Folkard, Beeston, all of United Kingdom

[73] Assignee: Medical Research Council, London, England

[21] Appl. No.: 549,858

[22] PCT Filed: Apr. 22, 1994

[86] PCT No.: PCT/GB94/00862

§ 371 Date: Oct. 20, 1995

§ 102(e) Date: Oct. 20, 1995

[87] PCT Pub. No.: WO94/25925

PCT Pub. Date: Nov. 10, 1994

[30] Foreign Application Priority Data

Apr. 27, 1993 [GB] United Kingdom ............ 9308715

[51] Int. Cl.⁶ .................................................. G06K 11/00

[52] U.S. Cl. ............................ 395/200.32; 324/337
[58] Field of Search .................... 364/514 R; 367/21,
367/27, 46, 53; 128/746; 324/333, 337,
356; 340/825.15; 73/620, 627, 645; 395/200.32

[56] References Cited

U.S. PATENT DOCUMENTS 4,922,362   5/1990   Miller et al. ............................ 367/46
4,964,103   10/1990  Johnson ................................ 367/53

*Primary Examiner*—James P. Trammell
*Assistant Examiner*—Thomas Peeso
*Attorney, Agent, or Firm*—Lee, Mann, Smith, McWilliams, Sweeney & Ohlson

[57] ABSTRACT

A method of and apparatus for the deconvolution of response data obtained from transmission of a maximum length sequence, wherein the samples of incoming data are deconvoluted and stored in a reconstruction buffer as said samples are received. It is possible in this way to employ a reconstruction buffer shorter than that necessary to store the complete deconvoluted waveform.

7 Claims, 4 Drawing Sheets

Fig. 1 PRIOR TECHNIQUE

TABLE

L = 3  
n = 3  
m = 2  
a = 1  
z = 1 rptr:    1  2  3  
R(rptr): 1  1  -1

| sample | Lcnt | ncnt | mcnt | mptr | rptr | wptr | RECOVERY WINDOW | | | | | |
|---|---|---|---|---|---|---|---|---|---|---|---|---|
| 0 (INIT. CONDS.) | 0 | 0 | 0 | 3 | 3 | 1 | 0 | 0 | 0 | 0 | 0 | 0 |
| 1 | 0 | 1 | 1 | 3 | 3 | 1 | -a | | | | | |
|   | 0 | 1 | 2 | 3 | 2 | 4 | | | | a | | |
| 2 | 0 | 2 | 1 | 3 | 3 | 2 | | -b | | | | |
|   | 0 | 2 | 2 | 3 | 2 | 5 | | | | | b | |
| 3 | 0 | 3 | 1 | 3 | 3 | 3 | | | -c | | | |
|   | 0 | 3 | 2 | 3 | 2 | 6 | | | | | | c |
| 4 | 1 | 1 | 1 | 1 | 1 | 1 | d | | | | | |
|   | 1 | 1 | 2 | 1 | 3 | 4 | | | | -d | | |
| 5 | 1 | 2 | 1 | 1 | 1 | 2 | | e | | | | |
|   | 1 | 2 | 2 | 1 | 3 | 5 | | | | | -e | |
| 6 | 1 | 3 | 1 | 1 | 1 | 3 | | | f | | | |
|   | 1 | 3 | 2 | 1 | 3 | 6 | | | | | | -f |
| 7 | 2 | 1 | 1 | 2 | 2 | 1 | g | | | | | |
|   | 2 | 1 | 2 | 2 | 1 | 4 | | | | g | | |
| 8 | 2 | 2 | 1 | 2 | 2 | 2 | | h | | | | |
|   | 2 | 2 | 2 | 2 | 1 | 5 | | | | | h | |
| 9 | 2 | 3 | 1 | 2 | 2 | 3 | | | i | | | |
|   | 2 | 3 | 2 | 2 | 1 | 6 | | | | | | i |

Fig. 4

DECONVOLUTION OF MLS RESPONSE DATA

This application is a 371 of PCT/GB94/00862 filed on Apr. 22, 1994.

FIELD OF THE INVENTION

This invention relates to a method of and apparatus for the deconvolution of response data obtained from transmission of maximum length sequences (MLS), similar sequences or variants of similar sequences. References to MLS hereinafter are intended to include such similar or variant sequences.

BACKGROUND OF THE INVENTION

The applicants' prior International patent application No PCT/GB93/00639, relates to the use of a maximum length sequence technique to record otoacoustic emissions. One field of application of the present invention is the deconvolution of response data in the technique proposed in the prior patent application. However, the present invention is not restricted to that field of application.

For signals that have to be extracted from noise, a conventionally applied method, as described in the prior patent application, is to stimulate with an MLS, record the response or incoming signal generated by that MLS and, using sampling techniques, store the received waveform in a memory buffer whose length is equal to the length of the MLS multiplied by the number of ADC samples that are required per MLS entry in order to avoid aliasing errors.

Another MLS is immediately delivered and its received waveform added to that already in the memory buffer. This process is continued until sufficient received waveforms have been added to improve the signal-to-noise ratio to an adequate degree.

The original response, or input signal, then has to be recovered by a deconvolution technique. One example of a suitable technique, proposed in the prior patent application, is as follows.

Let L equal the length of the MLS. The MLS represents stimuli that will be presented at a specified rate. If the minimum time between presentations of stimuli, corresponding to the elements in the MLS, is such that n samples are required to characterise the response or incoming signal then that period is known as a slice of the MLS and n is the number of samples in one slice. Once the responses to a set of MLSs have been recorded, as described above, then the resultant waveform is contained in a raw data buffer whose length is equal to nL. A reconstruction memory buffer, of equal length to the raw data buffer, is zeroed. The recovery sequence is then generated and comprises a 1 for every instance for which the MLS contains a 1 and a −1 for every occurrence of a zero in the original MLS. The data in the raw data buffer are then each multiplied by the first element in the recovery sequence. The product is added to the reconstruction buffer. The data in the raw data buffer are then rotated left by one slice. They are then each multiplied by the second element in the recovery sequence and again added to the reconstruction buffer. This operation is continued until all the elements in the recovery sequence have been used. The reconstruction buffer will then contain the original waveform deconvolved from the MLS. The procedure is illustrated in FIG. 1 of the accompanying drawings.

The disadvantages of the above-described deconvolution technique may be illustrated by an example using evoked otoacoustic emissions recorded with an MLS.

1. As the response is being averaged from noise then it is useful to be able to avoid the noisiest periods (excess noise) during the recording of the signal. Typically this is done by rejecting, that is not adding to the average, any periods of the response where the waveform recorded from the subject or patient exceeds a certain limit. However, as the stimulus is also recorded then, using conventional techniques, the stimulus period has to be excluded from this rejection criterion. With the MLS technique and the overlapping of stimuli and responses, it is not possible sensibly to apply the described rejection methods. This is a problem with using the above-described deconvolution technique for the MLS. The signal-to-noise ratio is poorer than it might otherwise be because periods of high noise activity have to be included in the average.

2. Without the use of a very large amount of processing power, no deconvolved waveform can be obtained until the entire averaging process is complete because errors will occur if the averaging procedure is interrupted in order to effect the deconvolution. This is because MLS samples will be missed, leading to errors in the reconstruction of the original waveform.

THE INVENTION

According to one aspect of the present invention, there is provided a method of deconvolution of response data obtained from transmission of a MLS (including similar and variant sequences as hereinbefore mentioned), according to which the samples of incoming data are deconvoluted and stored in a reconstruction buffer as they are received.

According to another aspect of the invention, there is provided apparatus for deconvolution of response data obtained from transmission of a MLS, comprising a reconstruction buffer and means for deconvoluting each sample of incoming data as it arrives and storing the deconvoluted sample in the reconstruction buffer.

For completeness, it should be mentioned that an MLS is a quasi-random binary sequence with strictly defined mathematical properties. Possible variants are Legendre sequences, M-pulse sequences and De Bruijn sequences.

In a development of the method and apparatus of the invention, means are provided to reject immediately any one or more reconstructed MLSS which are contaminated by noise in excess of a predetermined limit such that they should not be added to the average being collected in the reconstruction buffer.

A preferred technique for practising the invention comprises multiplying each sample in turn by the elements of the recovery sequence as the sample is received and immediately adding the product into corresponding positions in the reconstruction buffer.

The invention has the advantage that a raw data buffer memory, equal in size to the length of the MLS, is no longer required. As a result, it is possible to achieve substantial saving in the time required to carry out deconvolution and reconstruction of the original signal.

Furthermore, the reconstruction buffer need only be as large as the time window required to observe the final waveform. This means that said buffer can, in general, be very much shorter than the MLS. Thus, it is possible to transmit very long MLSs without the requirement for large buffers.

One field of application of the invention is in the recording of biological signals obtained as response data due to stimulation by a MLS. For example, in the testing of hearing, a MLS may be used to record Evoked Otoacoustic Emissions (EOAs) which constitutes the incoming response data. The original signal can then be recovered from this response data by the deconvolution method and apparatus in accordance with the invention.

The apparatus in accordance with the invention may comprise a digital signal processing board, a computer and controlling software.

Thus, according to another aspect of the invention, there is provided a digital signal processing board and a computer programmed to carry out deconvolution of the MLS by the method hereinbefore defined.

DESCRIPTION OF EMBODIMENT

The method and apparatus of the invention are exemplified in the following description, making reference to accompanying FIGS. 1 to 7, in which:

FIG. 4 is a table of values applicable to the flow diagram of FIG. 3 in one typical case.

Figure 1:
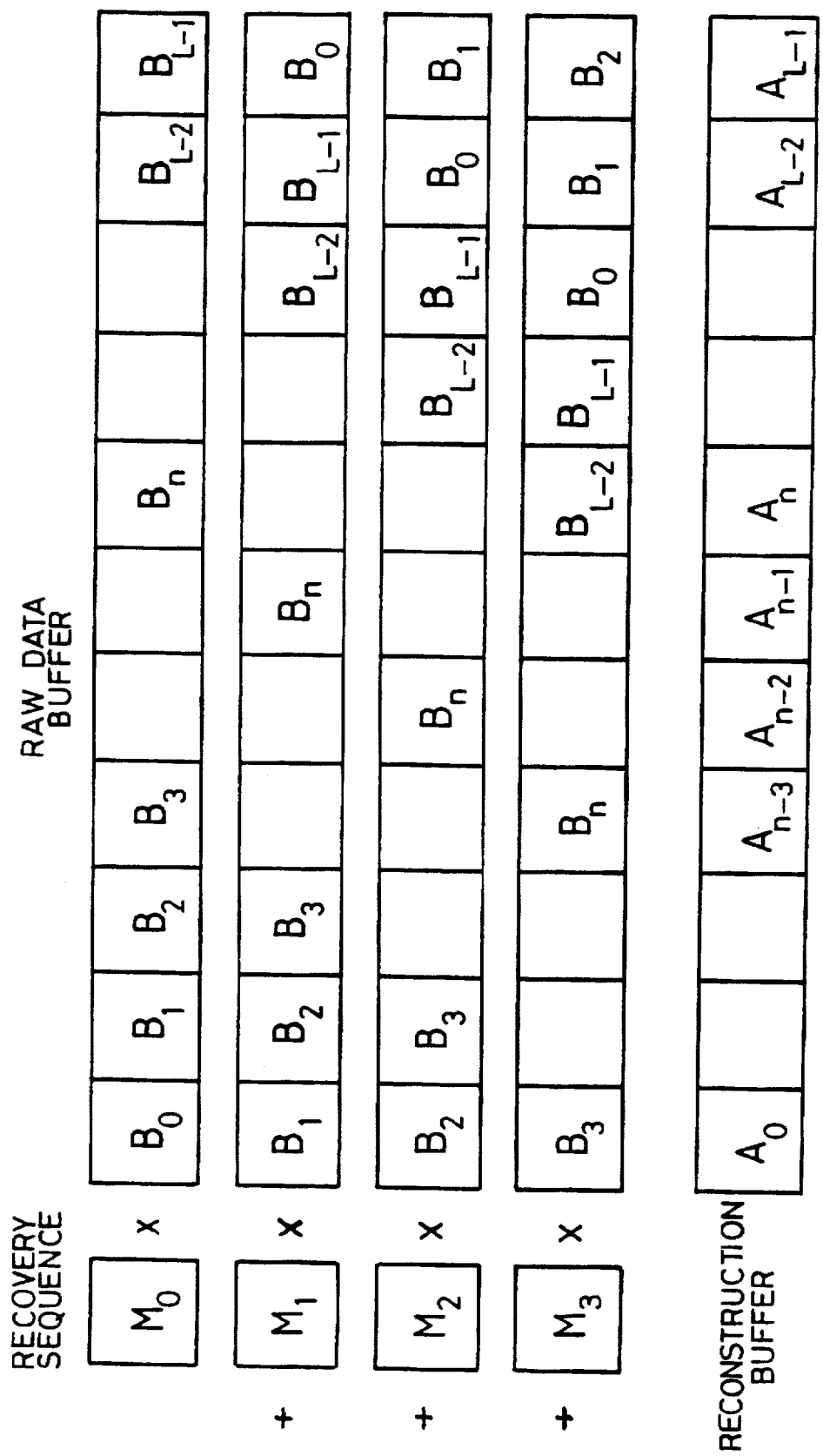
FIG. 1 illustrates a prior deconvolution technique.

A prior deconvolution technique is illustrated in FIG. 1. For an MLS of length L, the slices $B_0$ to $B_{L-1}$ of the incoming signal are averaged and stored in a raw data buffer. The values in the data buffer are then multiplied by the first element in the recovery sequence (Mo-Mn). The data from the raw data buffer are then added to the previously zeroed reconstruction buffer. The data in the raw data buffer are then rotated one place to the left, multiplied by the second element in the recovery sequence and added to the contents of the reconstruction buffer. This process is repeated until all distinct rotations of the raw data buffer have been completed (a total of L additions and L-1 rotations).

Figure 2:
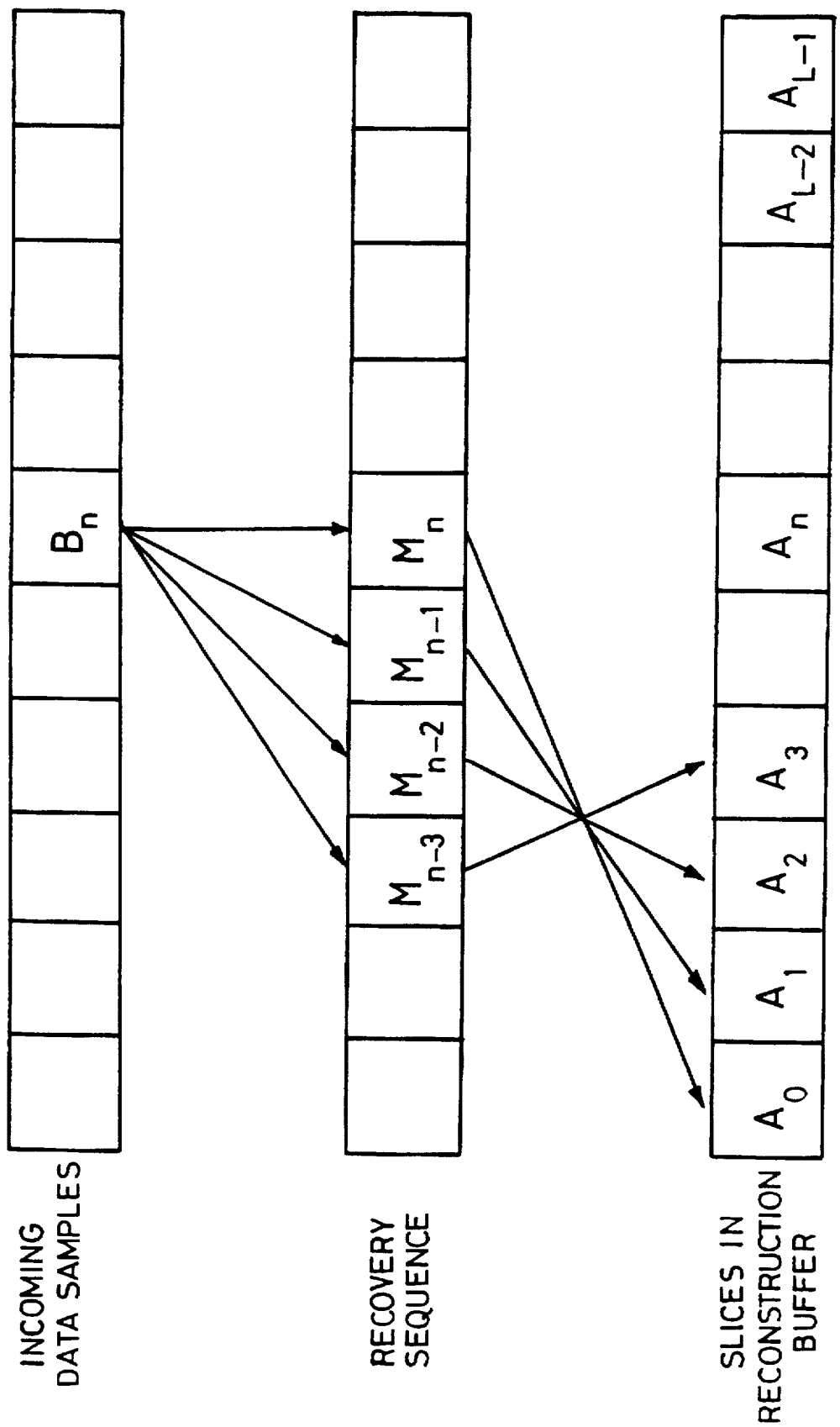
FIG. 2 illustrates the deconvolution technique in accordance with the invention.

From FIG. 1 it can be seen that samples initially stored in slice $B_n$ are ultimately added to $A_m$ after multiplying by $M_{n-m}$. In accordance with the invention, it has been realised that, instead of adding raw samples to B and then shifting, multiplying and adding into A, it is possible to simply multiply each raw sample in turn by the appropriate element M of the recovery sequence and add it directly to the corresponding positions in A. This will build up the reconstructed average directly from the incoming samples. This process is illustrated in FIG. 2.

This approach in accordance with the invention has several advantages:

1. With each incoming sample being dealt with on arrival there is no need to store the raw data samples for subsequent processing; the large raw data buffer B (of size nL) is thus dispensed with.

2. Only the R slices of A that span the required reconstruction window need to be stored, thus the memory required for the reconstruction buffer is reduced from nL to nR.

3. The number of operations performed on each sample is dependent on R rather than L, thus the processing load is reduced.

4. With both memory and processing requirements reduced, one can more readily use double-buffering techniques to generate a separate reconstruction for each presentation of the MLS sequence. Each reconstructed response can then be compared with a template and rejected if any value is too large. Acceptable responses can then be added into a summation buffer. The direct reconstruction approach thus makes real-time rejection of excess noise periods possible. This is a marked practical advantage for taking measurements where the time to record is limited primarily by the noise contamination on the signal.

Another way of explaining the technique in accordance with the invention is as follows.

Figure 3:
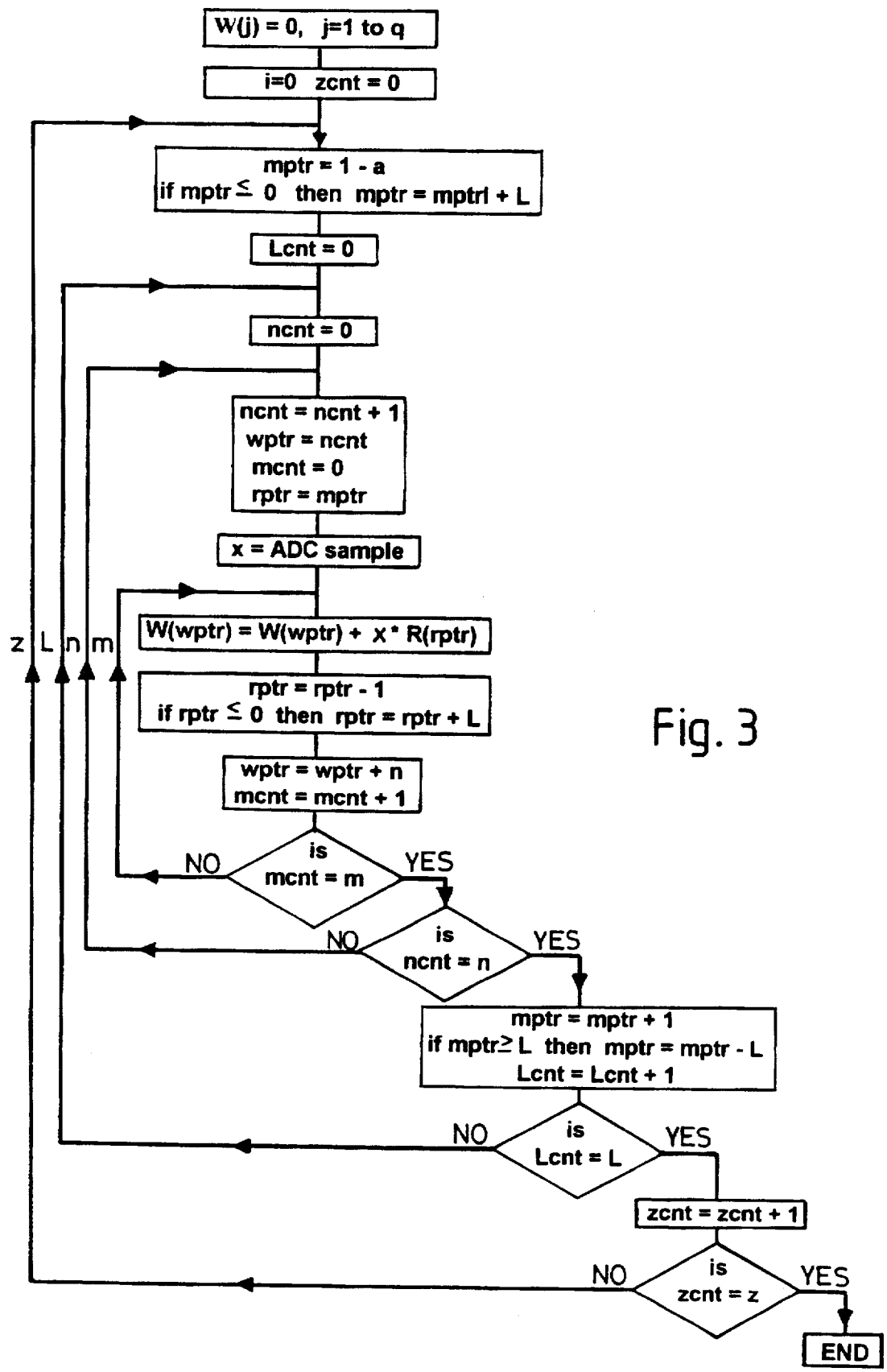
FIGS. 3 is a flow diagram illustrating the technique in accordance with the invention, when carried out using a recovery window shorter than the MLS.

FIG. 3 is a flow diagram illustrating an application of the technique in accordance with the invention when the recovery window or reconstruction buffer is shorter than the MLSS. The logical operations employed in the technique will be readily understood from the flow diagram, when this is read in conjunction with the following definitions:

| | |
|---|---|
| L | Length of MLS |
| n | Number of samples in one slice of the MLS |
| m | Number of slices in the recovery window |
| p | Number of samples in MLS (p = n*L) |
| x | ADC samples of the input (i = 1 to p) |
| q | Number of samples in the recovery window (q = m*n) |
| W(j) | Recovery window (j = 1 to q) |
| R(k) | Recovery sequence (= +1 or −1) (k = 1 to L) |
| a | Number of slices to start of recovery window |
| z | Number of MLS needed in average |
| mptr | Main recovery sequence pointer |
| rptr | Secondary recovery sequence pointer |
| wptr | Recording window pointer |

Further understanding will be gained from FIG. 4, which is a table of flow diagram values for one particular case in which one MLS has a length 3 and the recovery window starts after one slice and has a duration of two slices.

In principle, the illustrated technique, which may be referred to as MLS recovery "on the fly" is as follows:

Consider an MLS of length 3. This will have slices M1, M2 and M3 as shown in [A].

For the MLS in which M1=M2=1 and M3=0 the rotation and multiplication needed for conventional recovery are shown in [B].

| M1 | M2 | M3 | | | | | [A] |
|---|---|---|---|---|---|---|---|

```
   1  1  0       1        1  1  0      [B]
   1  0  1   ×   1    =   1  0  1
   0  1  1      −1        0 −1 −1
                      SUM: 2   0   0
```

In general, the multiplication and rotations are shown in [C]. It may not always be the case that the required recovery window will start at the start of the MLS and a case in which the recovery window has a delay of one slice from the start of the MLS is shown in [D].

```
   M1   M2   M3                              [C]
   M2   M3   M1
  −M3  −M1  −M2

M1   M2   M3                              [D]
   M2   M3   M1
  −M3  −M1  −M2
```

Now consider the same example as shown in [D] but with the individual ADC samples taken into the picture. The MLS is 1 1 0 with a recovery sequence R(k)=1 1 −1. Let there be three ADC samples per slice (n=3). The ADC samples in one MLS will be denoted by the letters a to i.

The MLS and the samples are shown in [E] and the matrix of samples that will make up the recovered waveform for the delayed recovery window, are shown in [F].

[E]

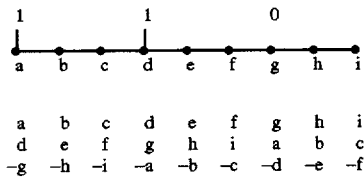

[F]
```
a  b  c  d  e  f  g  h  i
d  e  f  g  h  i  a  b  c
-g -h -i -a -b -c -d -e -f
```

The flow diagram and the accompanying table shows how the on-the-fly recovery algorithm can be used to obtained the desired, recovered waveform.

The invention is preferably realised using a digital signal processing board and a conventional computer. The software may be realised in any suitable language or code and, as an example, details of the routines FILLER and CHECKER which have been written in "C", to give an example of the coding involved, are as follows:

```
/*===============================================
FILLER - collect & deal with one sample
In actual use this would be an interrupt service routine, dealing with each
incoming sample. For each input sample a stimulus sample may be output,
depending on the value of the current MLS entry.
===============================================*/ void filler ( ) {
    float samp;                            // current input sample
    int n;
    int * mpr;                             // -> MLS entries
    mpr = &mls[sliceno];                   // -> MLS entry for current slice
    if (*mpr==1)                           // entry indicates stimulus?
        outsamp (outbuff[sampno]);         // yes- output stimulus sample
    samp = getsamp( );                     // get input sample
    for (n=0; n<rlen; n+=slen) {           // for each recon. slice
        currbuff [n+sampno] += samp * *mpr;  // add/subtract to current buffer
        mpr--;                             // move back through MLS . . .
        if (mpr < mls)
            mpr = &mls[mlslen-1];          // with wrap-around to end of MLS
    }
    sampno++;                              // count samples done within slice
    if (sampno < slen)
        return;                            // return if still within slice
                                           // start of new slice:-
    sampno = 0;                            // reset sample number
    sliceno++;                             // bump slice counter
    if (sliceno < mlslen)
        return;                            // return if not at end of MLS
                                           // end of MLS:-
    sliceno = 0;                           // reset slice counter
    toggle = !toggle;                      // switch reconstruction buffers
    currbuff = toggle ? recon1 : recon2;   // -> next buffer
    mlspnt = &mls[sliceno];                // Reset mls pointer to start of MLS
}
/*===============================================
CHECKER - process completed reconstructions
Checks to see if a buffer has completed being filled. If so, checks buffer
values against a rejection template and, if no values are too large, adds each
value into a summation buffer.
===============================================*/ int checker ( ) {
    int i;
    int ok;
    if (currbuff == prevbuff)              // has 'filler' finished a recon.?
        return (0);                        // no- wait some more
                                           // yes- 'prevbuff' points at it . . .
    ok = 1;
    for (i=0; i<rlen; i++)                 // check each value against template
        if (fabs(prevbuff[i]) > reject[i]) {
            ok = 0;
            break;
        }
    if (ok) {                              // all values passed-
        for (i=0; i<rlen; i++)
            summation[i] += prevbuff[i];   // add to summation buffer
        mlsdone++;                         // count good reconstructions
    }
    for (i=0; i<rlen; i++)                 // re-zero buff for next reconstruction
        prevbuff[i] = 0;
    prevbuff = currbuff;                   // update pointer
}
/*===============================================
MAIN
In practice 'checker' would be written to loop until enough good
```

-continued

```
reconstructions had been gathered, and would be continuously interrupted
by 'filler'. We simulate this here by placing both calls in a loop.
                                                                        */
main (int argc, char * argv[ ] ) {
  int i, n, n_needed;
  n_needed = 10;                    // ask for 10 reconstructions
  mls_init ( );                     // initialise variables, buffers, etc
  do {
    filler ( );
    checker ( );
  } while (mlsdone < n_needed);
  for (i=0; i<rlen; i+=4) {         // dump results
    for (n=0; n<4; n++)
      printf ("%15.4f", summation[i+n]);
    printf ("\n");
  }
}
```

We claim:

1. Apparatus for deconvolution of response data obtained from transmission of a maximum length sequence (MLS), comprising a reconstruction buffer, means for deconvoluting each sample of incoming data as it arrives and storing the deconvoluted sample in the reconstruction buffer, and means for multiplying each sample in turn by elements of a recovery sequence as the sample is received and immediately adding the product into corresponding portions in the reconstruction buffer.

2. Apparatus according to claim 1, in which means are provided to reject immediately any one or more reconstructed MLSs which are contaminated by noise in excess of a predetermined limit such that they should not be added to the average being collected in the reconstruction buffer.

3. Apparatus according to any of claim 1, in which the reconstruction buffer is only as large as the time window required to observe the final waveform.

4. Apparatus according to any of claims 1, which comprises a digital signal processing board, a computer and controlling software.

5. A method of deconvolution of response data obtained from transmission of a maximum length sequence (MLS), comprising the steps of a. deconvoluting samples of incoming data, b. storing said samples in a reconstruction buffer as said samples are received, c. creating a product by multiplying each said sample in turn by elements of a recovery sequence as said sample is received, and d. immediately adding said product into corresponding positions in said reconstruction buffer.

6. A method according to claim 5, applied to recording of biological signals obtained as response data due to stimulation by a MLS.

7. Apparatus comprising a digital signal processing board and a computer programmed to carry out deconvolution of the MLS by the method of any of claim 5.

* * * * *